US00PP24067P2

(12) United States Plant Patent
de Jong

(10) Patent No.: US PP24,067 P2
(45) Date of Patent: Dec. 3, 2013

(54) ***ASTRANTIA* PLANT NAMED 'STAR OF TREASURE'**

(50) Latin Name: ***Astrantia* spp. hybrid**
Varietal Denomination: Star of Treasure

(76) Inventor: Jacobus Robertus de Jong, Noordwijkerhout (NL)

( * ) Notice: Subject to any disclaimer, the term of this patent is extended or adjusted under 35 U.S.C. 154(b) by 100 days.

(21) Appl. No.: 13/506,293

(22) Filed: Apr. 9, 2012

(51) Int. Cl.
*A01H 5/00* (2006.01)

(52) U.S. Cl.
USPC ..... Plt./408

(58) Field of Classification Search
USPC ..... Plt./408
See application file for complete search history.

*Primary Examiner* — Susan McCormick Ewoldt
(74) *Attorney, Agent, or Firm* — Penny J. Aguirre

(57) ABSTRACT

A new cultivar of *Astrantia* 'Star of Treasure' characterized by its flowers that are lilac white with pink red markings, its flower bracts that are tipped with pink-red, and its relatively low and compact plant habit.

2 Drawing Sheets

Botanical classification: *Astrantia* spp. hybrid.
Variety denomination: 'Star of Treasure'.

RELATED APPLICATION

This application is co-pending with a U.S. Plant Patent applications filed for a cultivar derived from the same breeding program entitled *Astrantia* Plant Named 'Star of Passion' (U.S. Plant patent application Ser. No. 13/506,294).

BACKGROUND OF THE INVENTION

The present invention relates to a new and distinct cultivar of *Astrantia*, botanically of hybrid origin and known as *Astrantia* 'Star of Treasure' and will be referred to hereinafter by its cultivar name, 'Star of Treasure'.

The new cultivar originated from open pollination done by the Inventor in 1999 in Woubrugge, The Netherlands. Both the male and female parents were unnamed plants from the Inventor's breeding program. The specific parents are not known as seeds from various female plants were pooled. The Inventor selected 'Star of Treasure' as a single unique plant in 2010.

Asexual reproduction of the new cultivar was first accomplished by division by the Inventor in Woubrugge, The Netherlands in 2010. Propagation by division and tissue culture has determined that the characteristics of this cultivar are stable and are reproduced true to type in successive generations.

SUMMARY OF THE INVENTION

The following traits have been repeatedly observed and are determined to be the characteristics of 'Star of Treasure'. These characteristics in combination distinguish 'Star of Treasure' as a new and distinct cultivar of *Astrantia*.

1. 'Star of Treasure' exhibits flowers that are lilac white with pink red markings.
2. 'Star of Treasure' exhibits flower bracts that are tipped with pink-red.
3. 'Star of Treasure' exhibits a relatively low and compact plant habit; reaching about 70 cm in height.

'Star of Treasure' can be most closely compared to the cultivars 'Hadspen Blood' (not patented), 'Star of Beauty' (not patented) and 'Star of Passion'. 'Hadspen Blood' differs from 'Star of Treasure' in being taller in height and in having purple-pink flowers and bracts. 'Star of Beauty' differs from 'Star of Treasure' in having white flowers that have more purple coloration and in having bracts that are rosy purple on both surfaces. 'Star of Passion' differs from 'Star of Treasure' in having flowers that are grey white with dark purple tips and bracts that are dark purple on the lower surface.

BRIEF DESCRIPTION OF THE DRAWING

The accompanying colored photographs illustrate the overall appearance and distinct characteristics of a two-year old plant of the new *Astrantia* as field grown in de Hoef, The Netherlands (containerized for the photo).

The photograph in FIG. 1 provides a view of a typical flowering plant of 'Star of Treasure'.

Figure 1:
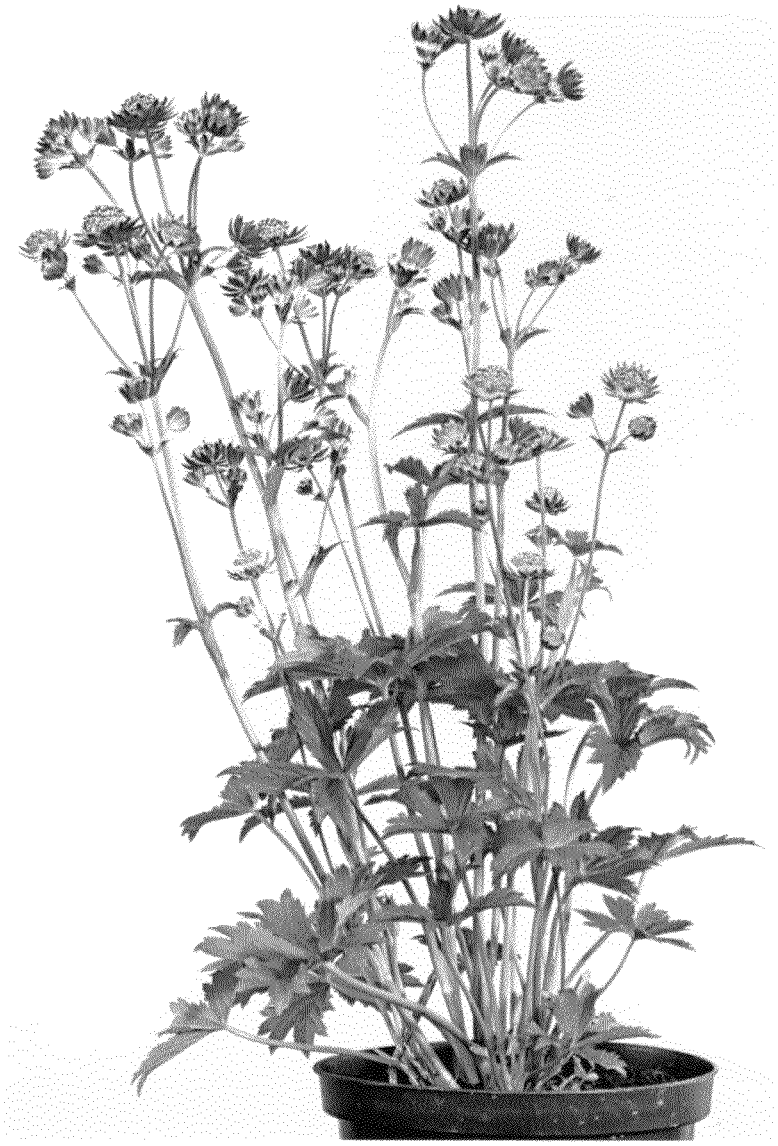
Figure 2:
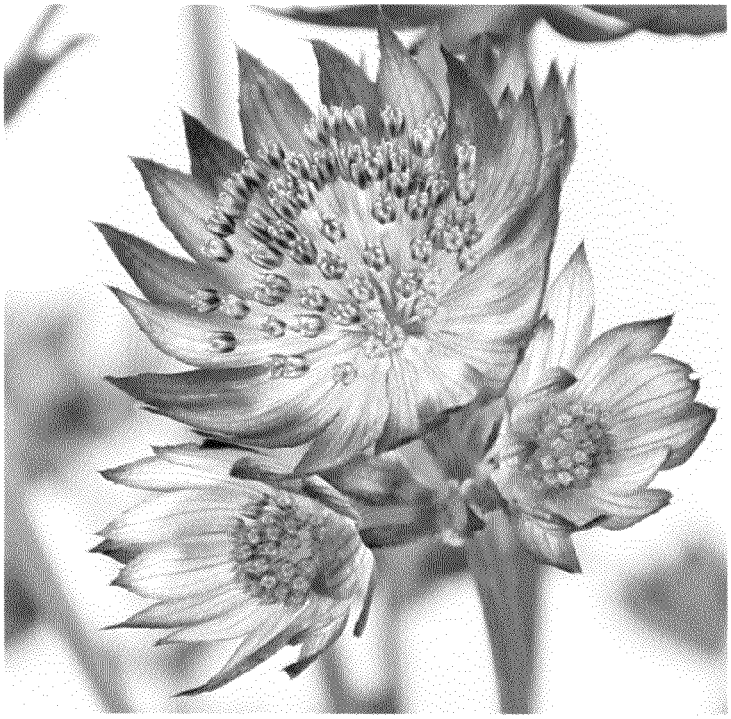

The photograph in FIG. 2 provides a close-up of the flowers 'Star of Treasure'.

Figure 3:
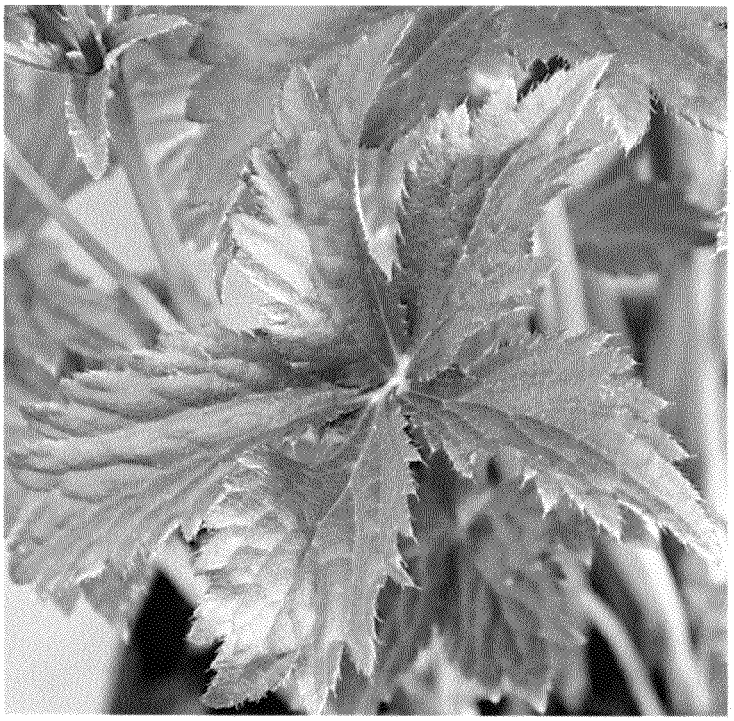

The photograph in FIG. 3 provides a close-up of a leaf 'Star of Treasure'. The colors in the photographs are as close as possible with the photographic and printing technology utilized. The color values cited in the detailed botanical description accurately describe the colors of the new *Astrantia*.

DETAILED BOTANICAL DESCRIPTION

The following is a detailed description of two-year-old plants of the new cultivar as field grown outdoors in De Hoef, Netherlands. Plants were grown under average day temperatures ranging from 15° to 28° C. and average night temperatures of 5° to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Herbaceous perennial.
*Blooming period*.—June to mid August in The Netherlands.
*Plant habit*.—Basal rosette with flowering stems growing from the base, ovate to broad oblong in shape.
*Height and spread*.—About 70 cm in height and 39.5 cm in diameter.
*Hardiness*.—Cold hardy at least to U.S.D.A Zone 6 and Heat tolerant at least to 30° C.
*Disease resistance*.—Not more susceptible to pests and diseases than other *Astrantia*.
*Root description*.—Dense, fine, well branched.
*Propagation*.—Tissue culture or division.
*Cropping time*.—19 weeks from a rooted propagule to finished field grown division.
*Growth rate*.—Moderate.

Stem description:
*Stem shape*.—Round.
*Stem color*.—144A.
*Stem size*.—Average of 31 cm in length (from base to lowest branching of inflorescence) and 5 mm in diameter.
*Stem surface*.—Slightly glossy, ribbed vertically.
*Stem strength*.—Strong.
*Branching habit*.—Stems grow freely from basal rosette, about 8 flowering stems.
*Internode*.—Average of 16.4 cm in length.

Foliage description:
*Leaf division*.—Simple.
*Leaf shape*.—Palamtely parted.
*Leaf base*.—Hastate, basal lobes of each leaf touching to slightly overlapping.
*Leaf apex*.—Acute.
*Leaf margin*.—Biserrate, teeth aristate.
*Leaf venation*.—Laciniate in pattern, upper veins; 143B, lower veins; 144B.
*Leaf attachment*.—Petiolate.
*Leaf arrangement*.—Most leaves grow as basal rosette, stem leaves are alternate.
*Leaf surface*.—Upper and lower surface; smooth and slightly glossy.
*Leaf color*.—Young upper surface; 143B, young lower surface; 144A to 144B, mature upper surface; 137A to 137B, lower surface; 146A to 146B.
*Leaf size*.—Basal leaves average 11.7 cm in length and 13.6 cm in width, stem leaves average 7.6 cm in length and 8.9 cm in width.
*Leaf number*.—Average of 34 leaves per plant, average of 18 are in the basal rosette.
*Petiole*.—Basal leaves; average 21.3 cm in length, 4 mm in height, 4 mm in width, ovate in shape, 144A in color, stem leaf; winged (sheathed), average of 4.0 cm in height, 3 mm in width.

Flower description:
*Inflorescence type*.—Compound umbel of numerous campanulate flowers subtended by showy involucral bracts.
*Lastingness of inflorescence*.—Average of 12 days, self cleaning.
*Inflorescence size*.—Terminal; average of 24.8 cm in height (including peduncle) and 14.3 cm in width, umbel; average of 2.1 cm in height and 4.1 cm in width.
*Inflorescence fragrance*.—Moderate, sweet, pleasant.
*Flower number*.—Average of 80 per umbel, average of 17 umbels per compound umbel, average of 1,350 flowers per flowering stem.
*Flower form*.—Umbel (compound).
*Flower aspect*.—Upright and upright-outward.
*Flower bud size*.—Average of 2 mm in length, average of 1.5 mm in diameter.
*Flower bud color*.—71BA, apex N155B, base 143A.
*Flower bud shape*.—Obovate with flattened apex.
*Flower size*.—Average of 4 mm in diameter and 1.1 cm in height.
*Corolla features*.—Petals are un-fused and upright.
*Petal number*.—5.
*Petal shape*.—Narrow ovate, incurved.
*Petal color*.—Opening and fully open upper and lower surfaces; 71A, apex N155B.
*Petal surface*.—Upper and lower surface; dull and smooth.
*Petal margins*.—Entire.
*Petal apex*.—Narrowly acute.
*Petal size*.—Average of 2 mm in length and 1 mm in width.
*Calyx form*.—Rotate, held upright.
*Calyx size*.—Average of 2 mm in length and 2 mm in diameter.
*Sepal number*.—5.
*Sepal shape*.—Narrow ovate.
*Sepal margin*.—Entire.
*Sepal size*.—Average of 2 mm length, 0.6 mm in width (at base).
*Sepal surface*.—Upper and lower surface; dull and smooth.
*Sepal apex*.—Broad acute.
*Sepal base*.—Cuneate.
*Sepal color*.—Young upper and lower surface; N189A apex 71B, mature upper and lower surface; N189A tinged 187A to 187B, apex 71B.
*Peduncle size*.—Average of 22.7 cm in length and 2.5 mm in diameter.
*Peduncle strength/aspect*.—Strong, terminals held upright, secondary held at an average of 35° from stem.
*Peduncle color*.—138A.
*Pedicel size*.—Average of 5 mm in length and 0.3 mm in width.
*Pedicel strength/aspect*.—Strong, terminal held upright, secondary held at 75°.
*Pedicel color*.—185D, apex 145D.
*Inflorescent leaves*.—About 5 per inflorescent, sessile, about 2.5 cm in length and 3.5 cm in width, palmately lobed with acute apex, entire margin and cuneate base, color 137A to 137B on upper surface and 146A to 146B on lower surface.

Involucral bracts:
*Bract number*.—About 20.
*Bract shape*.—Elliptic to narrow obovate.
*Bract size*.—About 2.1 cm in depth and 5 mm in width.
*Bract color*.—Upper surface; 70A, apex N189A, margins; 187A to 187B, lower surface; N186D, apex 187A.
*Bract texture*.—Both surfaces; dull and smooth.
*Bract apex*.—Acute, with two small teeth near the top.
*Bract base*.—Attenuate.
*Bract margins*.—Entire.

Reproductive organs:

*Gynoecium.*—2 pistils, about 3 mm in length, stigma is club-shaped and 187A in color, style is about 2.8 mm in length, between N187D and 71B in color, becoming lighter towards the base, ovary is 193A in color.

*Androcoecium.*—5 stamens, anthers are dorsifixed, elliptic in shape, about 0.5 mm in length and 187A in color, filament is about 4 mm in length, color; 155A, apex 71B, pollen is low in abundance and 156D in color.

*Fruit/seeds.*—No fruit set (or seeds) have been observed to date.

It is claimed:

1. A new and distinct cultivar of *Astrantia* plant named 'Star of Treasure' as herein illustrated and described.

* * * * *